United States Patent [19]

Mori et al.

[11] Patent Number: 5,441,888
[45] Date of Patent: Aug. 15, 1995

[54] PROCESS FOR PRODUCING D-MANDELIC ACID FROM BENZOYLFORMIC ACID

[75] Inventors: Takao Mori; Masakatsu Furui, both of Takatsuki; Katsuhiko Nakamichi, Sakai; Eiji Takahashi, Osaka, all of Japan

[73] Assignee: Tanabe Seiyaku Co., Ltd., Osaka, Japan

[21] Appl. No.: 142,914

[22] Filed: Oct. 29, 1993

[30] Foreign Application Priority Data

Nov. 5, 1992 [JP] Japan .................................. 4-295536

[51] Int. Cl.⁶ ....................... C12P 39/00; C12P 41/00; C12P 7/42; C12P 7/58
[52] U.S. Cl. ..................... 435/280; 435/42; 435/136; 435/146
[58] Field of Search ................. 435/42, 136, 146, 280

[56] References Cited

U.S. PATENT DOCUMENTS 4,622,301 11/1986 Günther et al. ............... 435/146
4,824,781 4/1989 Hummel et al. ............... 435/146

FOREIGN PATENT DOCUMENTS 3930104 4/1991 Germany .
57-198096 12/1982 Japan .
63-32492 2/1988 Japan .
4-341195 11/1992 Japan .

OTHER PUBLICATIONS

Christen Metal, J. Chem. Soc., Chem. Commun. pp. 264–266 (1988).
Tsuchiya S et al, Biotech Lett 14:1137–42 (1992).

*Primary Examiner*—Marian C. Knode
*Assistant Examiner*—S. Saucier
*Attorney, Agent, or Firm*—Browdy and Neimark

[57] ABSTRACT

There is disclosed a process for preparing D-mandelic acid comprising the steps of:

(1) treating racemic mandelic acid with a culture broth, cells or treated cells of a microorganism having ability of converting L-mandelic acid into benzoylformic acid.
(2) treating the reaction mixture of the step (1) with a culture broth, cells or treated cells of a microorganism having ability of stereoselectively reducing benzoylformic acid into D-mandelic acid, and
(3) isolating and collecting the D-mandelic acid from the reaction mixture.

12 Claims, No Drawings

PROCESS FOR PRODUCING D-MANDELIC ACID FROM BENZOYLFORMIC ACID

This invention relates to a novel process for preparing D-mandelic acid by using microorganisms.

D-Mandelic acid is useful compound as a raw material or synthetic intermediate for the preparation of pharmaceutical compounds such as antibiotics (e.g. penicillium-type or cephalosporin-type) or sympathetic nerve affecting drugs (e.g. ephedrin).

In the prior art, as the method for preparing D-mandelic acid, there have been known physical chemical methods, such as optical resolution by fractional crystallization, optical resolution by chromatography, or stereoselectively synthesizing methods in organic chemistry. However, these methods involve drawbacks, for example, that the operation is complicated or the yield and optical purity is low.

In addition, there have been known biochemical methods in which benzoylformic acid is stereoselectively reduced using microorganisms of the genus of Lactobacillus, Streptococcus or others (Japanese Patent First Publication (Kokai) No. 198096/1982, ditto No. 32492/1988). However, these methods have drawbacks, for example, that the optical purity of resulting D-mandelic acid is low.

The object of the invention is to provide an industrially advantageous process for preparing D-mandelic acid from racemic mandelic acid.

As a result of various investigations, the present inventors have found that D-mandelic acid could be efficiently prepared from racemic mandelic acid by using a microorganism having ability of convening L-mandelic acid into benzoylformic acid and a microorganism having ability of stereoselectively reducing benzoylformic acid into D-mandelic acid.

More specifically, this invention relates to the process for preparing D-mandelic acid which comprises the steps of:

(1) treating racemic mandelic acid with a culture broth, cells or treated cells of a microorganism having ability of convening L-mandelic acid into benzoylformic acid, (2) treating the reaction mixture of the step (1) with a culture broth, cells or treated cells of a microorganism having ability of stereoselectively reducing benzoylformic acid into D-mandelic acid, and (3) isolating and collecting the resultant D-mandelic acid from the reaction mixture.

Racemic mandelic acid is represented by the formula:

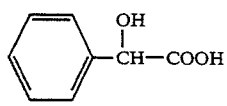

[I]

The racemic mandelic acid to be used as the starting material in the present invention may be not only one containing equal amounts of D-isomer and L-isomer, but one containing both of these optically active isomers in any ratio of mixture.

The microorganisms to be used in the present invention are microorganisms having the ability of converting L-mandelic acid into benzoylformic acid and microorganisms having the ability of reducing stereoselectively benzoylformic acid into D-mandelic acid. The microorganisms having said abilities may suitably be, for example, molds, bacteria, yeasts, and actinomycetes.

Suitable examples of the microorganisms having the ability of convening L-mandelic acid into benzoylformic acid include, for example, molds belonging to the genus of *Gibberella*, bacteria belonging to the genus of *Pseudomonas* or *Brevibacterium* and yeasts belonging to the genus of *Rhodotorula* or *Rhodosporidium*.

More specifically, such microorganisms may include, *Gibberella fujikuroi* IFO 5268, *Pseudomonas aeruginosa* ATCC 7700, ditto OUT 8252, *Pseudomonas fluorescens* IAM 1219, *Pseudomonas polycolor* IFO 3918, *Pseudomonas putida* ATCC 12633, *Brevibacterium ammoniagenes* IAM 1641, *Rhodotorula glutinis* IFO 0389, ditto IFO 0758, ditto IFO 0898, ditto OUT 6152, *Rhodotorula rubra* IFO 0001, ditto IFO 0918, ditto IFO 1100, ditto OUT 6158, *Rhodosporidium toruloides* IFO 0559, etc.

Suitable examples of the microorganisms having the ability of reducing stereoselectively benzoylformic acid into D-mandelic acid may include, for example, microorganisms belonging to the genus of *Micrococcus*, *Enterococcus* and *Streptomyces*, which were found by the inventors to have the above-mentioned ability. Moreover, microorganisms belonging to the genus of *Lactobacillus*, *Leuconostoc*, *Streptococcus*, *Nocardia*, *Proteus*, *Pseudomonas*, *Helicostylum*, *Pseudeurotium*, *Fusarium*, *Syncephalastrum* and *Cunninghamella*, which were mentioned in the Japanese First Patent Publication (Kokai) No. 198096/1982, may also be employed. Among them, microorganisms belonging to the genus of *Micrococcus* may be particularly preferable.

More specifically, such microorganisms may include *Micrococcus freudenreichii* No. 239 (FERM BP-4440), *Micrococcus luteus* No. 240 (FERM BP-4441), *Enterococcus faecalis* ATCC 11700, ditto ATCC 11420, ditto ATCC 12984, *Streptomyces lavendulae* IFO 3145, etc. Deposits under the Budapest Treaty of *Micrococcus freudenreichii* No. 239 and *Micrococcus luteus* No. 240 were made at National Institute of Biosciences and Human-Technology of the Agency of Industrial Science and Technology, the Ministry of International Trade and Industry, Chiba, Japan, as of Oct. 26, 1992, and have been assigned accession nos. FERM BP-4440 and FERM BP-4441, respectively.

The microorganisms to be used in the present invention may be either wild strains or mutant strains, and further may be those derived from these microorganisms according to the bioengineering methods such as gene recombination and cell fusion.

The cultivation of the above-mentioned microorganisms can be conducted in a culture medium conventionally used in this field of art, for example, a medium containing conventional carbon sources, nitrogen sources and inorganic salts, at pH of approximately 5 to 8, under aerobic condition at room temperature or under heating (preferably at 20° to 40° C.).

During the cultivation of the microorganism having the ability of convening L-mandelic acid into benzoylformic acid, racemic mandelic acid, in an amount of about 0.001% or more, particularly about 0.1 to 1%, may be added to the culture medium in order to enhance said ability.

The microbial cells of the microorganisms can be isolated and collected by conventional methods from the culture broth.

The treated product of such microbial cells (treated cells) may include lyophilized cells, acetone dried cells, extract of cells, self-digested cells, ground cells, sonicated cells. and enzymes purified by combination of known methods from the extract of microbial cells or culture broth.

Further, said microbial cells or treated cells in the present invention may be immobilized according to known methods, such as the polyacrylamide method, the sulfur containing polysaccharide gel method (e.g. carageenan gel method), the alginic acid gel method or the agar gel method, before use.

The step (1) in the present invention is the enzymatic reaction for converting the L-isomer included in the racemic mandelic acid into benzoylformic acid. The step (2) is the enzymatic reaction for stereoselectively reducing benzoylformic acid into D-mandelic acid. These steps can be performed suitably in an aqueous solution.

In the present invention, the enzymatic reactions of the steps (1) and (2) may be pedormed sequentially in order or simultaneously in a single pot.

In case of performing these reactions sequentially, the process may be practiced by, for example, (a) adding into the solution of racemic mandelic acid the culture broth, cells or treated cells of a microorganism having the ability of converting L-mandelic acid into benzoylformic acid, (b) carring out the enzymatic reaction to convert L-isomer into benzoylformic acid, (c), if necessary, removing the cells or treated cells from the reaction mixture, (d) adding the culture broth, cells or treated cells of a microorganism having the ability of stereoselectively reducing benzoylformic acid formed in the reaction mixture into D-mandelic acid, and (e) carring out the enzymatic reaction.

In case of performing the enzymatic reactions of step (1) and (2) simultaneously, the process may be practiced by, for example, (a) adding into the solution of racemic mandelic acid the culture broth, cells or treated cells of a microorganism having the ability of converting L-mandelic acid into benzoyl formic acid along with a microorganism having the ability of stereoselectively reducing benzoylformic acid into D-mandelic acid, and (b) carrying out the enzymatic reaction to convert L-mandelic acid into D-mandelic acid via benzoylformic acid.

The concentration of the starting material (i.e., racemic mandelic acid) in the reaction mixture may be generally 0.05~10%(W/V), particularly 0.5~5% (W/V). The reactions of the step (1) and (2) will proceed suitably at room temperature or under heating, preferably at 10°~50° C., particularly at 25°~40° C. The pH of the reaction mixture may be adjusted preferably at 4~10, particularly at 6~9, during the reactions of both the step (1) and (2).

In addition, it is preferable to carry out the enzymatic reaction of the step (2) in the presence of glucose. The concentration of glucose in the reaction mixture may be preferably about 0.1~10% (W/V).

In case of using living cells, it is preferred to carry out the enzymatic reaction in the presence of a surfactant in order to reduce the whole reaction period of time. The surfactant used for this purpose may include, for example, cetylpyridinium bromide, cetyltrimethylammonium bromide, p-isooctylphenyl ether (commercial name: Triton-X, manufactured by Röhm and Haas, U.S.A.). The concentration of the surfactant in the reaction mixture may be preferably about 0.0001~0.1% (W/V).

The reactions, if necessary, may be carried out simultaneously with the cultivation of the microorganisms. In this case, the reaction along with the cultivation can be conducted under the same conditions as cultivation using a culture medium to which the substrate is added in advance.

The step (3) which is the step for isolation of D-mandelic acid from the reaction mixture, can be carried out by conventional methods. For example, crystals of D-mandelic acid can be collected by removing the undissolved materials, such as microbial cells, from the reaction mixture, acidifying said reaction mixture followed by extraction using an adequate solvent (e.g. ethyl acetate), and concentrating the extract under reduced pressure.

According to the present invention, D-mandelic acid can be efficiently produced in high yield and high purity from racemic mandelic acid by the combination of the reaction using microorganisms having the ability of converting benzoylformic acid into D-mandelic acid, and the reaction using microorganisms having the ability of stereoselectively reducing benzoylformic acid into D-mandelic acid.

In addition, in case of performing said two reactions simultaneously, benzoylformic acid, which inhibits the reaction of convening L-mandelic acid into benzoylformic acid, will be rapidly convened into D-mandelic acid without accumulating in the reaction mixture. Consequently the reaction proceeds efficiently to give D-mandelic acid in high yield.

The present invention is further illustrated in more detail by the following Examples but should not be construed to be limited thereto. In the following Examples, "%" used for the concentration indicates "weight / volume (g /dl)".

Example 1

Production of D-mandelic acid from racemic mandelic acid by performing the first step for converting L-isomer into benzoylformic acid and the second step for convening benzoylformic acid into D-mandelic acid sequentially in order:

A medium (pH7.0, 100 ml) containing 0.5% of DU-mandelic acid, 1.0% of polypeptone, 1.0% of yeast extract, 0.5% of sodium chloride was charged into a 500 ml volume shaking flask and sterilized at 120° C. for 10 minutes. A loopful of *Pseudomonas polycolor* IFO 3918 was inoculated into said medium, and cultivated at 30° C. for 20 hours under shaking. The resultant culture broth (900 ml) was centrifuged to collect the microbial cells. The cells were suspended in physiological saline and collected by centrifugation to obtain the washed cells (hereinafter referred to as Microbial cells 1).

Separately, a medium (pH7.0, 100 ml) containing 1.25% of yeast extract, 1.0% of meat extract, 0.5% of glucose, 1.0% of polypeptone, 0.5% of sodium chloride was charged into a 500 ml volume shaking flask and sterilized at 120° C. for 10 minutes. A loopful of *Micrococcus freudenreichii* No. 239 was inoculated into the medium and cultivated at 30° C. for 20 hours. The resultant culture broth (3400 ml) was centrifuged to collect the microbial cells. The cells were suspended in physiological saline and collected by centrifugation to obtain the washed cells (hereinafter referred to as Microbial cells 2).

To the above-mentioned Microbial cells 1 were added 960 ml of 50 mM—phosphate buffer (pH7.0) containing 15.9 g of DL-mandelic acid and the reaction was carried out by stirring at 30° C. for 24 hours. The obtained reaction mixture was centrifuged to remove the cells and give supernatant. Into said supernatant were added the above-mentioned Microbial cells 2, 50 ml of phosphate buffer (pH7.0) and 50 ml of 40% glucose solution, and the reaction was carried out at 30° C. for 24 hours. The obtained reaction mixture was centrifuged to remove the cells and give supernatant.

Said supernatant was adjusted to pH 1.0 with hydrochloric acid, followed by adding 2000 ml of ethyl acetate and carring out extraction. The ethyl acetate phase was collected and concentrated under reduced pressure to obtain the crude crystals of D-mandelic acid. To the crude crystals was added, hexane: ethyl acetate (1:1) solvent and the crystals were dissolved by heating and then recrystallized by cooling to obtain 9.52 g of crystals of D-mandelic acid.

Specific rotation $[\alpha]_D^{20} - 155.4°$ (c=1, H$_2$O)
Optical purity: 100%

Example 2

Production of D-mandelic acid from racemic mandelic acid by performing the first step for converting L-isomer into benzoylformic acid and the second step for converting benzoylformic acid into D-mandelic acid simultaneously:

*Pseudomonas polycolor* IFO 3918 and *Micrococcus freudenreichii* No.239 were cultured in the same manner as described in Example 1. Respectively 50 ml and 500 ml of the each culture broth were mixed, and then centrifuged to collect the cells. Said cells were suspended in physiological saline and collected by centrifugation to obtain washed cells.

To said washed cells were added 100 ml of 200 mM phosphate buffer (pH7.0) containing 1.52 g of DL-mandelic acid, and the reaction was carried out by stirring at 30° C. for 48 hours. During the reaction, 1% glucose solution was added to the reaction mixture continuously (5 ml/hour), while keeping the pH of the reaction mixture around 7.0 by addition of 5N NaOH solution. The amount of the optically active isomer in the reaction mixture was measured by high performance liquid chromatography (HPLC) by the use of a chiral cell (SUMI-CHIRAL OA-5000, manufactured by Sumitomo Kagaku Bunseki Center) (hereinafter the same). As the result, it was found that 1.22 g of D-mandelic acid was accumulated in the reaction mixture.

Example 3

Conversion of benzoylformic acid into D-mandelic acid using microorganisms of the genus of *Micrococcus* and *Enterococcus*:

A medium (pH7.0, 3 ml) containing 1.25% of yeast extract, 1.0% of meat extract, 0.5% of glucose, 1.0% of polypeptone, and 0.5% of NaCl was charged into a test tube and sterilized at 120° C. for 10 minutes. A loopful of microorganism shown in Table 1 was inoculated into said medium and cultivated at 30° C. for 24 hours. To the obtained culture broth was added 0.3 ml of phosphate buffer (pH7.0) containing 24.8 mg of benzoylformic acid, 25.1 mg of D-mandelic acid and 5.5% of glucose and reaction was carried out for 24 hours.

The amount of benzoylformic acid and D-mandelic acid in the reaction mixture were measured by HPLC. The results are shown in Table 1.

TABLE 1

| Microogranism employed | Amount of benzoylformic acid in the reaction mixture (mg) | Amount of D-mandelic acid in the reaction mixture (mg) |
| --- | --- | --- |
| *Micrococcus freudenreichii* No. 239 | 7.0 | 41.8 |
| *Micrococcus luteus* No. 240 | 7.0 | 41.3 |
| *Enterococcus faecalis* ATCC 11700 | 13.2 | 36.8 |
| *Enterococcus faecalis* ATCC 12984 | 17.8 | 30.1 |

Example 4

Production of D-mandelic acid from benzoylformic acid using *Micrococcus freudenrechii* No.239:

A medium (pH7.0, 100 ml) containing 1.25% of yeast extract, 1.0% of meat extract, 0.5% of glucose, 1.0% of polypeptone, and 0.5% of NaCl was charged into a 500 ml volume shaking flask and sterilized at 120° C. for 10 minutes. A loopful of *Micrococcus freudenreichii* No.239 was inoculated into said medium, and cultivated at 30° C. for 20 hours under shaking. The obtained culture broth (1000 ml) was centrifuged to collect the microbial cells. Said cells were suspended in physiological saline and collected by centrifugation to obtain washed cells.

To said washed cells were added 400 ml of 0.2M phosphate buffer (pH7.0) containing 6 g of benzoylformic acid and 4% of glucose and the reaction was carried out at 30° C. for 48 hours. The obtained reaction mixture was centrifuged to remove the cells.

The thus-obtained supernatant was adjusted to pH 1.0 with hydrochloric acid, followed by adding 1000 ml of ethyl acetate and carring out extraction. The ethyl acetate phase was collected and concentrated under reduced pressure to obtain 5.52 g of the crude crystal of D-mandelic acid. To the crude crystals was added hexane: ethyl acetate (1:1) solvent and the crystals were dissolved by heating and then recrystallized by cooling to obtain 5.16 g of crystals of D-mandelic acid.

Specific rotation $[\alpha]_D^{20}: -155.9°$ (C=1, H$_2$O)
Optical purity: 100%

What we claim is:

1. A process for preparing D-mandelic acid which comprises the steps of:
   (1) treating racemic mandelic acid with a culture broth or cells of a first microorganism having the ability of converting L-mandelic acid into benzoylformic acid, said first microorganism being selected from the group consisting. of *Gibberella fujikuroi*, *Pseudomonas aeruginosa*, *Pseudomonas fluorescens*, *Pseudomonas polycolor*, *Pseudomonas putida*, *Brevibacterium ammoniagenes*, *Rhodotorula glutinis*, *Rhodotorula rubra*, and *Rhodosporidium toruloides;*
   (2) treating the reaction mixture of the step (1) with a culture broth or cells of a second microorganism having the ability of stereoselectively reducing benzoylformic acid into D-mandelic acid, said second microorganism being selected from the group consisting of *Micrococcus freudenreichii*, *Micrococcus luteus*, *Enterococcus faecalis*, and *Streptomyces lavendulae;* and
   (3) isolating and collecting the D-mandelic acid from the reaction mixture.

2. The process according to claim 1 wherein the steps (1) and (2) are carried out sequentially in order.

3. The process according to claim 1 wherein the steps (1) and (2) are carried out simultaneously in a single pot.

4. The process according to claim 1 wherein said first microorganism is *Pseudomonas polycolor*.

5. The process according to claim 1 wherein said second microorganism is *Micrococcus freudenreichii* or *Micrococcus luteus*.

6. The process according to claim 1 wherein said second microorganism is *Micrococcus freudenreichii* No. 239 (FERM BP-4440), or *Micrococcus luteus* No. 240 (FERM BP-4441).

7. The process according to claim 1 wherein
 (a) said microorganism in step (1) is selected from the group consisting of *Gibberella fujikuroi* IFO 5268, *Pseudomonas aeruginosa* ATCC 7700, *Pseudomonas fluorescens* IAM 1219, *Pseudomonas polycolor* IFO 3918, *Pseudomonas putida* ATCC 12633, *Brevibacterium ammoniagenes* IAM 1641, *Rhodotorula glutinis* IFO 0389, *Rhodotorula glutinis* IFO 0758, *Rhodotorula glutinis* IFO 0898, *Rhodotorula rubra* IFO 0001, *Rhodotorula rubra* IFO 0918, *Rhodotorula rubra* IFO 1100, and *Rhodosporidium toruloides* IFO 0559, and
 (b) said second microorganism is selected from the group consisting of *Micrococcus freudenreichii* No. 239 (FERMBP-4440), *Micrococcus luteus* No. 240 (FERMBP-4441), *Enterococcus faecalis* ATCC 11700, *Enterococcus faecalis* ATCC 11420, *Enterococcus faecalis* ATCC 12984, and *Streptomyces lavendulae* IFO 3145.

8. A process for producing D-mandelic acid which comprises the steps of:
 treating benzoylformic acid with a culture broth or cells of a microorganism having the ability of stereoselectively reducing benzoylformic acid into D-mandelic acid, and
 isolating and collecting the resultant D-mandelic acid from the reaction mixture, said microorganism being *Micrococcus freudenreichii* or *Micrococcus luteus*.

9. The process according to claim 8 wherein said microorganism is *Micrococcus freudenreichii* No. 239 (FERM BP-4440) or *Micrococcus luteus* No. 240 (FERM BP-4441).

10. The process according to claim 1 wherein said cells of the first microorganism are cells being selected from the group consisting of lyophilized cells, acetone dried cells, extract of cells, self-digested cells, ground cells and sonicated cells.

11. The process according to claim 1 wherein said cells of the second microorganisms are cells being selected from the group consisting of lyophilized cells, acetone dried cells, extract of cells, self-digested cells, ground cells and sonicated cells.

12. The process according to claim 8 wherein said cells are cells being selected from the group consisting of lyophilized cells, acetone dried cells, extract of cells, self-digested cells, ground cells and sonicated cells.

* * * * *